(12) United States Patent
Pianca et al.

(10) Patent No.: US 9,492,655 B2
(45) Date of Patent: Nov. 15, 2016

(54) STIMULATION SYSTEM WITH PERCUTANEOUSLY DELIVERABLE PADDLE LEAD AND METHODS OF MAKING AND USING

(75) Inventors: Anne Margaret Pianca, Santa Monica, CA (US); Christopher B. Gould, Valencia, CA (US); Joel Adam Krueger, Stillwater, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1864 days.

(21) Appl. No.: 12/428,978

(22) Filed: Apr. 23, 2009

(65) Prior Publication Data

US 2009/0270957 A1  Oct. 29, 2009

Related U.S. Application Data

(60) Provisional application No. 61/048,102, filed on Apr. 25, 2008.

(51) Int. Cl.
*A61N 1/00* (2006.01)
*A61N 1/05* (2006.01)

(52) U.S. Cl.
CPC .................. *A61N 1/0553* (2013.01)

(58) Field of Classification Search
USPC ................................ 607/116, 117
See application file for complete search history.

(56) References Cited

U.S. PATENT DOCUMENTS

| | | |
|---|---|---|
| 6,181,969 B1 | 1/2001 | Gord |
| 6,249,707 B1 * | 6/2001 | Kohnen et al. ............. 607/117 |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,795,737 B2 | 9/2004 | Gielen et al. |
| 6,999,820 B2 | 2/2006 | Jordan |
| 7,089,057 B2 | 8/2006 | Heathershaw et al. |
| 7,191,018 B2 | 3/2007 | Gielen et al. |

(Continued)

FOREIGN PATENT DOCUMENTS

| | | |
|---|---|---|
| EP | 1 048 271 A2 | 11/2000 |
| EP | 1 048 317 A2 | 11/2000 |

(Continued)

OTHER PUBLICATIONS

U.S. Appl. No. 11/863,034, filed Sep. 27, 2007.

(Continued)

*Primary Examiner* — Christopher D Koharski
*Assistant Examiner* — Nadia A Mahmood
(74) *Attorney, Agent, or Firm* — Lowe Graham Jones PLLC; Bruce E. Black

(57) ABSTRACT

An implantable lead includes an expandable paddle body and a plurality of electrodes disposed on the paddle body. The electrodes are configured and arranged to provide electrical stimulation to adjacent tissue when implanted and the lead is coupled to a control module. The paddle body is configured for percutaneous implantation through an introducer followed by expansion of a volume of the paddle body by at least 10%. Alternatively, the paddle body is configured for percutaneous implantation and when implanted the lead is configured and arranged so that a position or orientation of the plurality of electrodes relative to the paddle body can be altered.

16 Claims, 5 Drawing Sheets

(56) References Cited

U.S. PATENT DOCUMENTS

| | | | |
|---|---|---|---|
| 7,212,867 B2* | 5/2007 | Van Venrooij et al. | 607/116 |
| 7,244,150 B1 | 7/2007 | Brase et al. | |
| 7,254,445 B2 | 8/2007 | Law et al. | |
| 7,369,894 B2 | 5/2008 | Gerber | |
| 2001/0023367 A1* | 9/2001 | King et al. | 607/117 |
| 2001/0053885 A1* | 12/2001 | Gielen et al. | 604/20 |
| 2002/0022873 A1* | 2/2002 | Erickson et al. | 607/117 |
| 2003/0204228 A1 | 10/2003 | Cross et al. | |
| 2004/0049240 A1 | 3/2004 | Gerber et al. | |
| 2004/0059392 A1 | 3/2004 | Parramon et al. | |
| 2004/0193228 A1 | 9/2004 | Gerber | |
| 2004/0236381 A1 | 11/2004 | Dinsmoor et al. | |
| 2004/0236382 A1 | 11/2004 | Dinsmoor et al. | |
| 2004/0243208 A1 | 12/2004 | Jordan | |
| 2005/0010260 A1 | 1/2005 | Gerber | |
| 2005/0015117 A1 | 1/2005 | Gerber | |
| 2005/0033372 A1 | 2/2005 | Gerber | |
| 2005/0033373 A1 | 2/2005 | Gerber | |
| 2005/0033374 A1 | 2/2005 | Gerber | |
| 2005/0033393 A1 | 2/2005 | Daglow | |
| 2005/0070969 A1 | 3/2005 | Gerber | |
| 2005/0113877 A1 | 5/2005 | Spinelli et al. | |
| 2005/0113878 A1 | 5/2005 | Gerber | |
| 2005/0246004 A1 | 11/2005 | Cameron et al. | |
| 2005/0288758 A1* | 12/2005 | Jones et al. | 607/116 |
| 2005/0288759 A1 | 12/2005 | Jones et al. | |
| 2006/0069415 A1 | 3/2006 | Cameron et al. | |
| 2006/0161235 A1 | 7/2006 | King | |
| 2007/0060991 A1 | 3/2007 | North et al. | |
| 2007/0073357 A1 | 3/2007 | Rooney et al. | |
| 2007/0150007 A1 | 6/2007 | Anderson et al. | |
| 2007/0150036 A1 | 6/2007 | Anderson | |
| 2007/0179579 A1 | 8/2007 | Feler et al. | |
| 2008/0004674 A1 | 1/2008 | King et al. | |
| 2008/0004675 A1 | 1/2008 | King et al. | |
| 2008/0046036 A1 | 2/2008 | King et al. | |
| 2008/0071320 A1 | 3/2008 | Brase | |
| 2008/0103534 A1 | 5/2008 | Gerber | |
| 2008/0103569 A1 | 5/2008 | Gerber | |
| 2008/0103574 A1 | 5/2008 | Gerber | |
| 2008/0140168 A1 | 6/2008 | Walter et al. | |
| 2008/0228250 A1* | 9/2008 | Mironer | 607/117 |
| 2008/0243220 A1 | 10/2008 | Barker | |
| 2008/0294211 A1 | 11/2008 | Moffitt | |
| 2009/0012591 A1 | 1/2009 | Barker | |
| 2009/0112282 A1 | 4/2009 | Kast et al. | |

FOREIGN PATENT DOCUMENTS

| | | |
|---|---|---|
| EP | 1 048 271 B1 | 11/2006 |
| EP | 1 818 074 B1 | 4/2009 |
| WO | WO-03/090851 A2 | 11/2003 |
| WO | WO-2005/016447 A2 | 2/2005 |
| WO | WO-2005/030323 A1 | 4/2005 |
| WO | WO-2005/079911 A1 | 9/2005 |
| WO | WO-2006/047264 A1 | 5/2006 |
| WO | WO-2006/047265 A1 | 5/2006 |
| WO | WO-2006/047291 A2 | 5/2006 |
| WO | WO-2006/113593 A2 | 10/2006 |
| WO | WO-2006/119135 A2 | 11/2006 |
| WO | WO-2006/135791 A2 | 12/2006 |
| WO | WO-2007/087626 A2 | 8/2007 |
| WO | WO-2008/005142 A1 | 1/2008 |
| WO | WO-2008/005144 A2 | 1/2008 |
| WO | WO-2008/005153 A2 | 1/2008 |
| WO | WO-2008/054443 A1 | 5/2008 |
| WO | WO-2008/055097 A2 | 5/2008 |
| WO | WO-2008/100841 A1 | 8/2008 |
| WO | WO-2008/115754 A1 | 9/2008 |
| WO | WO-2009/042172 A2 | 4/2009 |

OTHER PUBLICATIONS

U.S. Appl. No. 11/855,033, filed Sep. 13, 2007.

* cited by examiner

STIMULATION SYSTEM WITH PERCUTANEOUSLY DELIVERABLE PADDLE LEAD AND METHODS OF MAKING AND USING

CROSS REFERENCE TO RELATED APPLICATION

This application claims the benefit of U.S. Provisional Patent Application Ser. No. 61/048,102, filed Apr. 25, 2008, the entire contents of which is incorporated by reference.

FIELD

The present invention is directed to the area of devices and methods for stimulation of tissue using an array of electrodes, as well as methods of making and using the devices. In addition, the present invention is directed to the area of devices and methods for stimulation of tissue using a percutaneously deliverable paddle lead.

BACKGROUND

Stimulation systems have been developed to provide therapy for a variety of disorders, as well as for other treatments. For example, stimulation systems can be used in neurological therapy by stimulating nerves or muscles, for reducing pain in certain populations of patients by stimulating the spinal cord, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

A stimulation system can include a control module (with a pulse generator), one or more leads, and an array of electrodes on the lead(s). The electrodes are in contact with, or near, the nerves, muscles, or other tissue to be stimulated. The pulse generator in the control module generates electrical pulses that are delivered by the electrodes to body tissue. For example, electrical pulses can be provided to the dorsal column fibers within the spinal cord to provide spinal cord stimulation.

Implantation of conventional stimulation systems may include invasive procedures such as a laminotomy or laminectomy. This invasive surgery typically requires surgical training and can be time consuming and costly.

BRIEF SUMMARY

One embodiment is an implantable lead including an expandable paddle body and a plurality of electrodes disposed on the paddle body. The electrodes are configured and arranged to provide electrical stimulation to adjacent tissue when implanted and the lead is coupled to a control module. The paddle body is configured for percutaneous implantation through an introducer followed by expansion of a volume of the paddle body by at least 10%.

Another embodiment is an implantable lead including a paddle body and a plurality of electrodes disposed on the paddle body. The electrodes are configured and arranged to provide electrical stimulation to adjacent tissue when implanted and the lead is coupled to a control module. The paddle body is configured for percutaneous implantation and when implanted the lead is configured and arranged so that a position or orientation of the plurality of electrodes relative to the paddle body can be altered.

Yet another embodiment is a method for percutaneous implantation of a lead of an electrical stimulation system. An introducer is inserted through skin of a patient with at least a portion of the lead disposed in the introducer. The lead includes a paddle body with a plurality of electrodes disposed on the paddle body. The lead is positioned near the tissue to be stimulated. The introducer is withdrawn leaving the lead implanted in the patient. The volume of the paddle body is expanded by at least 10% after implanting the lead.

A further embodiment is a kit for implanting a lead including a lead with a paddle body and a plurality of electrodes disposed on the paddle body. The kit also includes an introducer having a non-circular, closed-path, transverse cross-section through which the paddle body of the lead can be percutaneously implanted into tissue of a body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

FIG. 5A shows the electrodes in the closed position and FIG. 5B shows the electrodes in the open position;

FIG. 7A shows the image if the electrodes are positioned correctly and FIG. 7B shows the image if the electrodes are positioned incorrectly, according to the invention.

DETAILED DESCRIPTION

The present invention is directed to the area of devices and methods for stimulation of tissue using an array of electrodes, as well as methods of making and using the devices. In addition, the present invention is directed to the area of devices and methods for stimulation of tissue using a percutaneously deliverable paddle lead.

The paddle leads described herein are preferably percutaneously implantable. This may obviate the need for performing an invasive procedure such as a laminotomy or laminectomy for implantation of the paddle lead.

Figure 1:
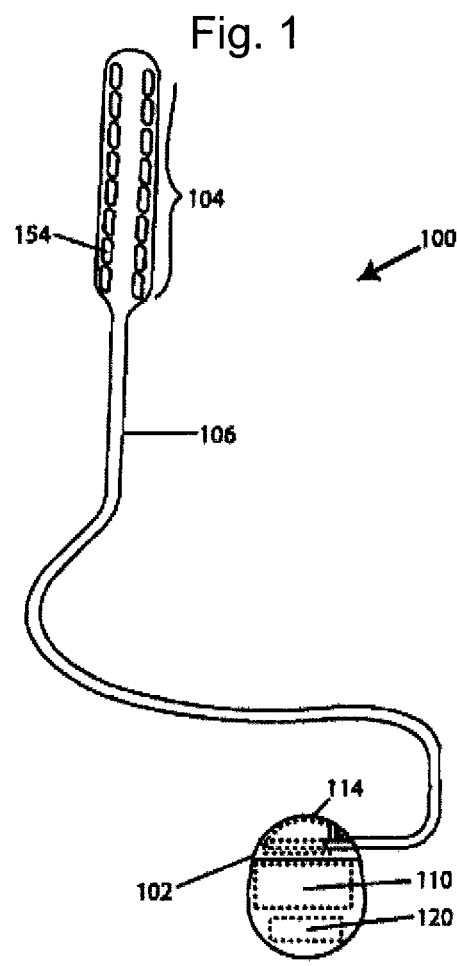
FIG. 1 is a schematic illustration of one embodiment of a stimulation system, according to the invention.
Figure 2:
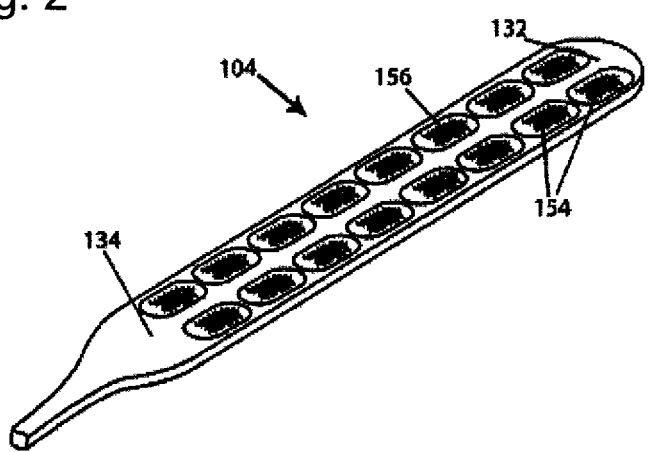
FIG. 2 is a schematic perspective top view of one embodiment of a paddle body, according to the invention.

FIG. 1 illustrates schematically one embodiment of a stimulation system 100. The stimulation system includes a control module (e.g., a stimulator or pulse generator) 102 and a lead 106 that includes a paddle body 104. The paddle body 104 typically includes an array of electrodes 154 as illustrated, for example, in both FIGS. 1 and 2. The surface 156 of the electrodes 154 are typically exposed on a surface 132 of the lead 106, as illustrated in FIG. 2. The control module 102 typically includes an electronic subassembly 110 and optional power source 120 disposed in a sealed housing 114. The control module 102 typically includes a connector into which the proximal end of the lead body 106 can be plugged to make an electrical connection via conductive contacts on the control module 102 and on the lead body 106. It will be understood that the system for stimulation can include more, fewer, or different components and can have a variety of different configurations including those configurations disclosed in the stimulation system references cited herein. Examples of stimulation systems with electrode leads are found in, for example, U.S. Pat. Nos. 6,181,969; 6,516,227; 6,609,029; 6,609,032; 6,741,892, and 7,244,150; and U.S. patent applications Ser. Nos. 11/319,291; 11/396,309; 11/532,844; 11/609,586; 11/692,772; 11/773,867; 11/855,033; and 11/863,034, all of which are incorporated by reference.

The stimulation system or components of the stimulation system, including one or more of the lead 106, the paddle body 104 and the control module 102, are typically implanted into the body. The stimulation system can be used for a variety of applications including, but not limited to, brain stimulation, neural stimulation, spinal cord stimulation, and the like.

The electrodes 154 can be formed using any conductive material. Examples of suitable materials include metals, alloys, conductive polymers, conductive carbon, and the like, as well as combinations thereof. The number of electrodes 154 in the array of electrodes 154 may vary. For example, there can be two, four, six, eight, ten, twelve, fourteen, sixteen, or more electrodes 154. As will be recognized, other numbers of electrodes 154 may also be used. The electrodes can be arranged in any suitable configuration including an array with two or more columns. For example, FIG. 1 illustrates an array of electrodes including two columns. The columns of electrodes can be aligned with each other or staggered. Any other regular or irregular array of electrodes can be used.

Conductors 190 (FIGS. 6A and 6B—only one conductor is illustrated for purposes of clarity) are attached to each of the electrodes 154 on the distal end of the lead 106 and extend along the lead 106 to terminals (not shown) on the proximal end of the lead 106. The conductors may connect one or more electrodes 154 to each terminal. In at least some embodiments, each electrode is coupled to a different terminal by a separate conductor. The terminals on the lead can then be connected with contacts on the control module 102 to conduct electrical pulses from the control module to the electrodes 154.

The lead 106, including the portion 134 (FIG. 2) of the paddle body 104 disposed around the electrodes 154. The portion 134, as well as a lead body of the lead 106, is typically made of a biocompatible, non-conductive material such as, for example, silicone, polyurethane, polyetheretherketone (PEEK), epoxy, and the like. Optionally, the lead may include one or more lumens through which the conductors pass or through which a drug or other medication can pass to an opening in the lead near the electrodes 154.

One embodiment of a lead 106 includes a paddle body 104 that can be delivered percutaneously through an introducer, such as a needle introducer, because the paddle body is made of a material that can be expanded after delivery. In at least some embodiments, the expansion of the paddle body is an expansion in the volume occupied by the paddle body by at least 10%, 15%, 25%, 40%, 50%, 75%, 100%, 150%, 200%, or more.

In some embodiments, the paddle body 104 includes a mesh or other compactable material incorporated into the wall(s) of the paddle body 104. The mesh can be constructed using a conductive or non-conductive (non-conductive is preferred) biocompatible material such as polyester (e.g., Dacron™), polyurethane, stainless steel, or nitinol. The paddle lead can be introduced into the epidural space using, for example, a standard introducer needle and procedure. Upon placement in the epidural space the mesh or other compactable material is expanded. In one embodiment, the paddle body with mesh/compactable material is constrained within an introducer. For example, the paddle body 104 may be folded or otherwise compacted to fit through an introducer. Upon correct placement in the epidural space the introducer is removed and the mesh/compactable material expands to form the paddle body 104 of the lead.

Figure 3A:
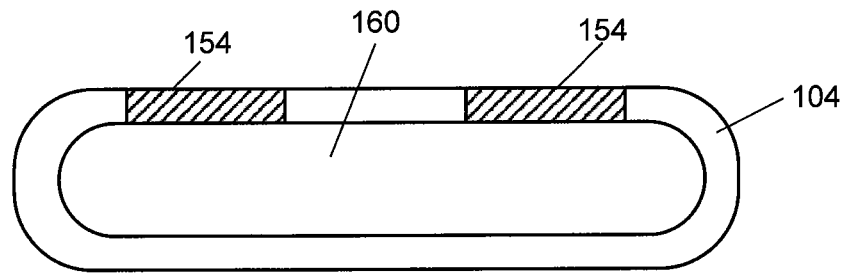
FIGS. 3A and 3B are schematic cross-sectional views of one embodiment of a paddle body in expanded (FIG. 3A) and collapsed (FIG. 3B) states, according to the invention.
Figure 3B:
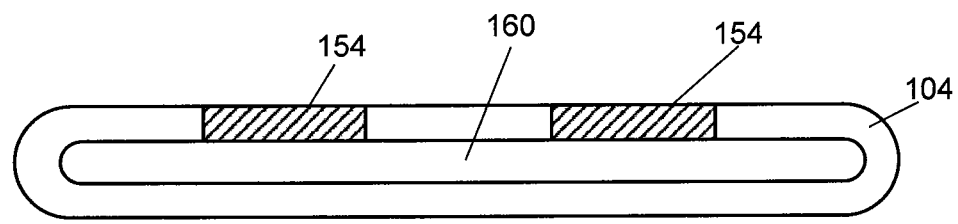

FIG. 3A schematically illustrates a cross-section of another embodiment of an expandable paddle body 104. The paddle body 104 includes at least one interior lumen 160 that is in fluid communication with one or more lumens (not shown) of the lead 106. In at least some embodiments, the paddle body 104 can include a mesh, as described above, or a stetchable polymer material that that is incorporated into the wall(s) of the paddle body 104 of the lead. In other embodiments, the paddle body 104 is simply sufficiently flexible to collapse without pressure in the lumen. The paddle lead can be introduced into the epidural space in the collapsed state, as illustrated in FIG. 3B, using, for example, a standard introducer needle and procedure. Upon placement in the epidural space the paddle body 104 is expanded through the use of pressure directed through one or more lumens in the lead and the lumen 160. For example, the interior lumen 160 may be opened or inflated with a fluid such as air, saline, polyurethane, silicone, or other suitable gases or liquids. It will be recognized that a paddle body 104 may include more than one interior lumen 160. In addition to facilitating expansion of the paddle body, the interior lumen may provide a path for conductors individually attached to one or more electrodes and extending from the electrodes through the lead to terminals at the proximal end of the lead.

Optionally, the interior lumen 160 may also be deflatable. For at least some embodiments, the inflated portion of the lead may remain inflated for a predetermined period of time and then deflate. For example, the interior lumen 160 of the lead may remain inflated for sufficient time to allow fibrotic tissue to form around the paddle body over, for example, 4 to 6 weeks. After remaining inflated for the predetermined time period the interior lumen may deflate over time. This embodiment may be particularly useful for stabilizing the paddle body of the lead during the acute in-growth stages of fibrotic tissue formation. Alternatively or additionally, a practitioner may deflate the paddle body by removal of at least a portion of the fluid in the paddle body. In some embodiments, when the interior lumen deflates the paddle body assumes geometry similar to that of a cylindrical percutaneous lead, which can be removed using less invasive surgical procedures compared to those typically used to remove a standard paddle lead. In at least some embodiments, the paddle body may be inflated and deflated and re-inflated and re-deflated as desired.

In at least some embodiments, the introducer that is used to percutaneously implant the lead may include a needle with a non-circular, closed-path, transverse cross-section to facilitate implantation of the paddle body 104 of the lead 106. For example, an introducer needle with a rectangular or elliptical cross-section, or any combination thereof (e.g., a generally rectangular shape with rounded corners), that permits passage of, or conforms to the shape of, the paddle body 104 of the lead 106 could be utilized. Examples of non-circular, closed path, transverse cross-sections for an introducer needle are illustrated in FIGS. 4B-4E and compared to a circular introducer needle cross-section illustrated in FIG. 4A. Examples of possible relative dimensions of the introducer are also provided in FIGS. 4A-4E where the inner diameter of the cylindrical needle introducer in these Figures is Y. It will be understood that other relative dimensions can be used for the size of the needle introducers. The term "closed-path" means that a complete path, starting at a point and returning to that point, can be made around the transverse cross-section without reversing direction and retracing a portion of the path. For example, U-shaped and V-shaped cross-sections are not closed-path.

Typically, the introducer has a cross-sectional size that permits removal of the introducer leaving the lead in the patient. In at least some embodiments, the entire lead 106 may have a non-circular cross-section which may reduce one (e.g., the vertical) dimension of the needle. For example, the entire lead may have a rectangular or elliptical cross section. These introducer shapes may result in the use of smaller incision or less tissue trauma.

Figure 5A:
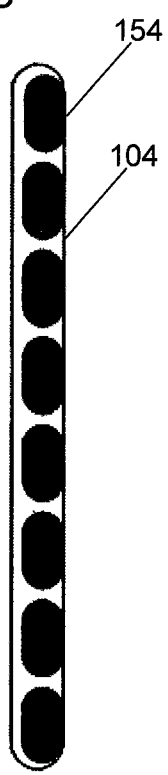
FIGS. 5A and 5B are schematic top views of a paddle lead that has electrodes with hinges that facilitate reversible deployment, according to the invention, where
Figure 5B:
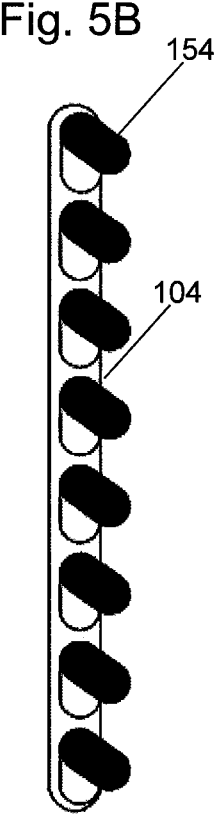

FIGS. 5A and 5B illustrate yet another embodiment of a lead 106 that includes a paddle body 104 with multiple electrodes 154. It will be recognized that arrays of electrodes other than the array illustrated in FIGS. 5A and 5B can be used including arrays with multiple columns of electrodes. In this embodiment, at least a portion of the electrodes are configured so that, when implanted, a position or orientation of the electrodes can be altered. FIG. 5A illustrates the configuration of the electrodes during insertion of the lead into a patient. One or more of the electrodes 154 are hinged so that upon insertion and positioning within the patient, the electrodes 154 can be rotated on the hinge(s) as illustrated in FIG. 5B. Preferably, the rotation is reversible to facilitate explantation of the lead. This arrangement may also produce expansion of the paddle body 104 by the new position of the electrodes themselves or by the electrodes pushing on surrounding parts of the paddle body 104 causing them to stretch.

In one embodiment, prior to implantation of the lead a stylet is inserted into a lumen in the lead. The stylet interacts electrically or mechanically with contacts in the lead to cause the electrodes to be in the first position as illustrated in FIG. 5A. When the stylet is removed and no longer interacts with the contacts, the electrodes then move to the second position as illustrated in FIG. 5B. Alternatively, the stylet can be permanently or removably disposed in the lead and coupled to the electrodes so that rotational or longitudinal (within the lead) movement of the stylet changes the orientation of the electrodes between the two positions illustrated in FIGS. 5A and 5B. As yet another alternative, the stylet can be inserted into the lead after implantation causing the position or orientation of the electrodes 154 to change.

Alternatively, the position of the electrodes can be altered using a fluid, instead of a stylet, that is injected into the lumen of the lead before, after, or during implantation to mechanically alter the position or orientation of the electrodes. For example, the fluid may interact with mechanical contacts or pressure points within the lead to cause the electrodes to alter position or orientation.

In other embodiments, the paddle body 104 can be disposed within a removable sheath prior to implantation to hold the electrodes in the position illustrated in FIG. 5A. After implantation, the sheath can be removed and the electrodes then rotate to the position illustrated in FIG. 5B. The sheath may be removed entirely from the lead or may be moved proximally along the lead to expose the paddle body 104. In some embodiments, the sheath may be moved back over the paddle body 104 to return the electrodes to the position illustrated in FIG. 5A.

In yet other embodiments, the electrodes may be coupled to a wire, cam, stylet, or the like which is in turn coupled to a proximal end of the lead. The proximal end of the lead can be turned to move the electrodes from the position illustrated in FIG. 5A to the position illustrated in FIG. 5B (or any intermediate position) using the wire. In at least some embodiments, the proximal end of the lead can be turned in the opposite direction to move the electrodes in the opposite way or to relieve tension on the electrodes or wire. Alternatively, an external handle or other mechanism can be coupled to the wire, cam, or stylet (instead of, or in addition to, the proximal end of the lead) to alter the orientation of the electrodes. The handle may be detachable from the wire and the wire may be detachable from the electrodes or lead.

Figure 6A:
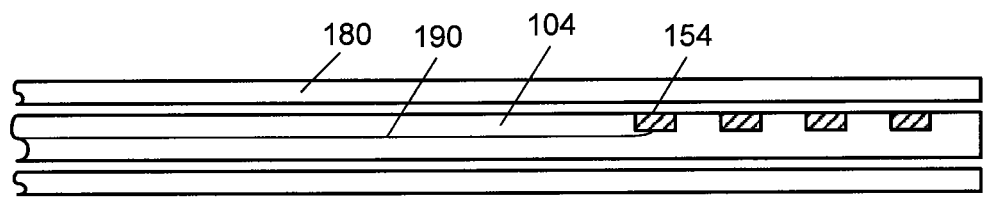
FIG. 6A is a schematic cross-sectional view of one embodiment of a paddle lead disposed in a needle introducer, according to the invention.
Figure 6B:
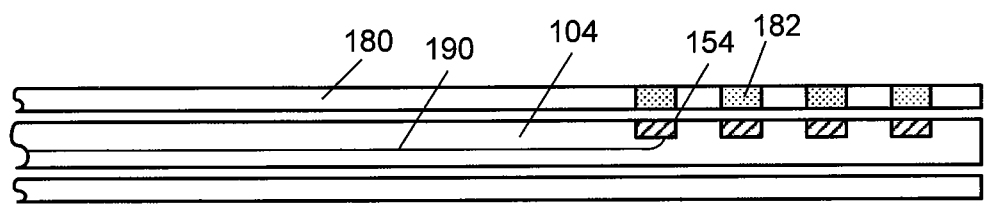
FIG. 6B is a schematic cross-sectional view of one embodiment of a paddle lead disposed in a needle introducer with windows, according to the invention.
Figures 4A, 4B, 4C, 4D, 4E:
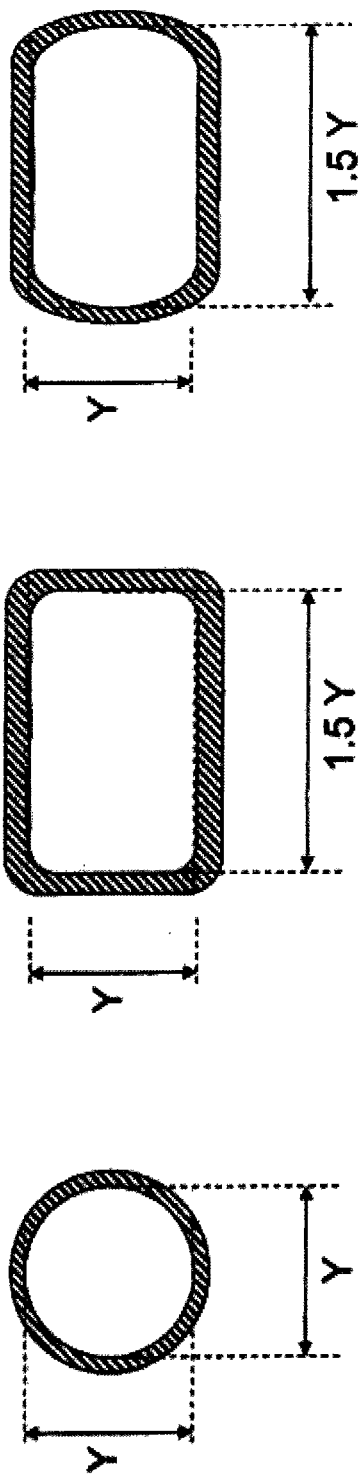
FIGS. 4A-4E are schematic cross-sectional views of individual embodiments of introducer needles for percutaneously introducing a paddle lead into a patient, according to the invention, where FIG. 4A.

In any of the preceding embodiments, the needle introducer may include one or more open windows in the introducer that can be aligned with one or more of the electrodes. FIG. 6A illustrates in cross-section one embodiment of a needle introducer 180 with a portion of the paddle body 104, and corresponding electrodes 154, disposed in the introducer. FIG. 6B illustrates another embodiment of a needle introducer 180 that includes window 182 cut out of the introducer 180 to permit contact between tissue and the electrodes 154 of the paddle body 104. This arrangement can allow confirmation of correct position of the electrodes, via trial stimulation and patient feedback, before the introducer is withdrawn and the paddle body of the lead is allowed to expand into the paddle configuration. It will be recognized that there may be one window for each electrode or there may be fewer or more windows than electrodes. For example, the needle introducer may only include one or two windows that are aligned with only one or two of the electrodes of the paddle body. It will also be recognized that the size of the windows need not correspond to the size of the electrodes. The windows may be larger, smaller, or the same size as the electrodes. In some embodiments, a single window may be sized to expose more than one electrode and may even expose one or more columns of electrodes.

In at least some embodiments, the proximal end of the paddle body is sufficiently tapered so that the needle introducer can be repositioned, if necessary, over the paddle body. This would allow for multiple insertions through one or more needle sticks. This arrangement may also facilitate explantation using a needle introducer.

Figure 7A:
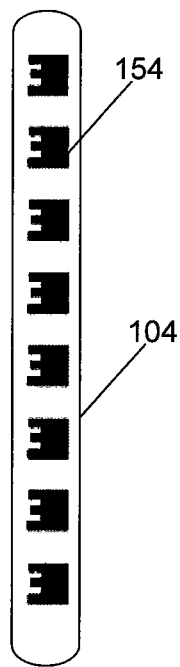
FIGS. 7A and 7B depict schematically fluoroscopic images generated from a paddle body with a one or more electrodes with an identification feature where
Figure 7B:
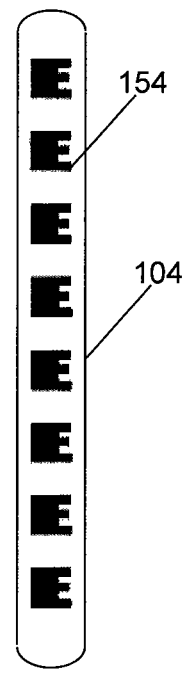

In at least some embodiments, one or more of the electrodes include an identification feature, such as a shape that is asymmetric about at least one axis to permit orientation of the lead to be confirmed without direct visual inspection, such as through the use of fluoroscopy, for example. During or after implantation it is desirable to confirm that the lead 106 and, particularly, the electrodes 154 are in the correct orientation. At least one electrode includes an identification feature that allows a medical practitioner to confirm that the paddle is positioned in the correct orientation (e.g., the active surface area of the electrodes is facing the dura mater.) The electrodes can be made of a material that can be imaged through the surrounding tissue using methods such as, for example, fluoroscopy, x-ray imaging, or magnetic resonance imaging. FIGS. 7A and 7B illustrate images of electrodes with identification features where the electrodes are correctly (FIG. 7A) or incorrectly (FIG. 7B) oriented. It will be recognized that not all of the electrodes need to have this feature. It will also be recognized that features may be arranged on the same or different electrodes so that the orientation in two or more directions (e.g., lateral and transverse) can be identified.

Returning to FIG. 1, the control module 102 typically includes a housing 114 with an electronic subassembly 110 and, in at least some embodiments, a power source 120 disposed within a chamber in the housing. Preferably, the housing is resistant to moisture penetration into the chamber containing the electronic subassembly and power source.

Figure 8:
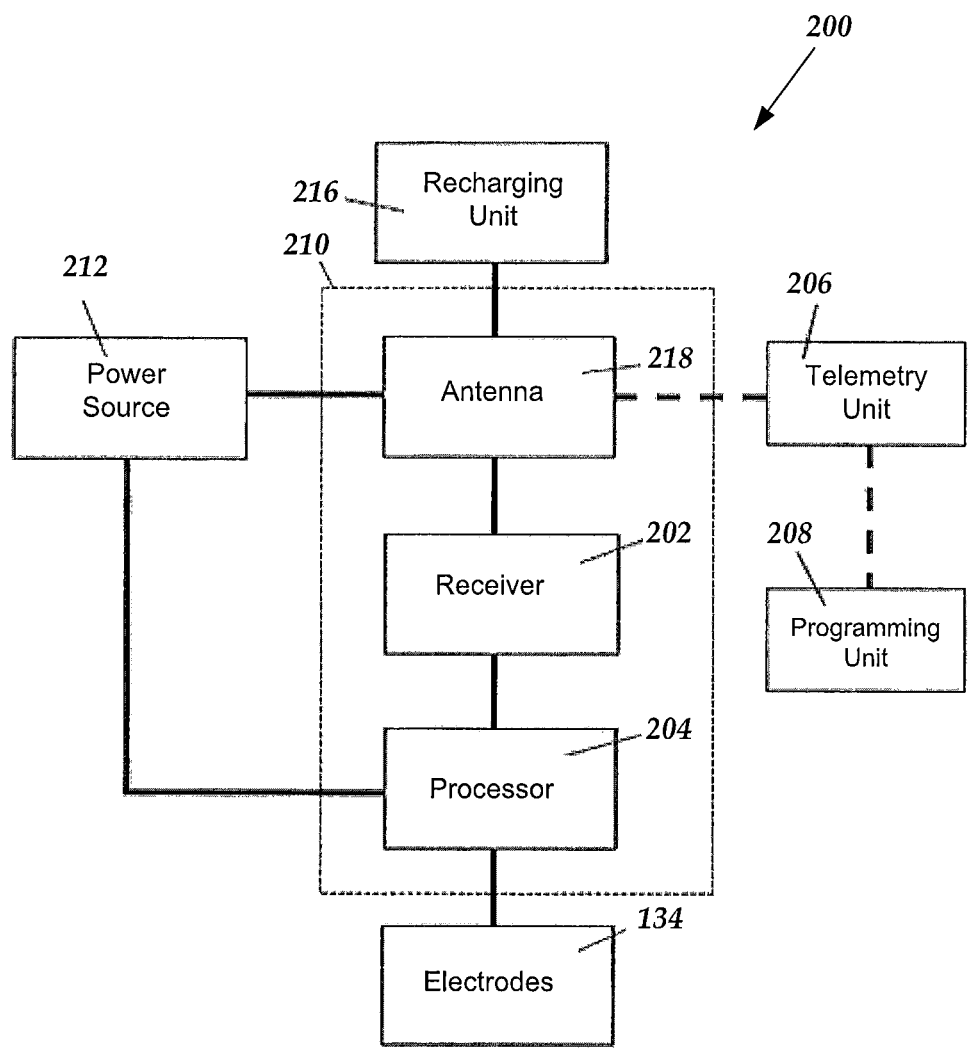
FIG. 8 is a schematic overview of components of one embodiment of a system for stimulation, according to an embodiment of the invention.

FIG. 8 is a schematic overview of one embodiment of components of a stimulation system 200 including an electronic subassembly 210 disposed within a control module. It will be understood that the stimulation system can include more, fewer, or different components and can have a variety of different configurations including those configurations disclosed in the stimulator references cited herein.

Some of the components (for example, power source 212, antenna 218, receiver 202, and processor 204) of the stimulation system can be positioned on one or more circuit boards or similar carriers within a housing of an implantable pulse generator, if desired. Any power source 212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 218 or a secondary antenna. The external power source can be in a device that is mounted on the skin of the user or in a unit that is provided near the user on a permanent or periodic basis.

If the power source 212 is a rechargeable battery, the battery may be recharged using the optional antenna 218, if desired. Power can be provided to the battery for recharging by inductively coupling the battery through the antenna to a recharging unit 216 external to the user. Examples of such arrangements can be found in the references identified above.

In one embodiment, electrical current is emitted by the electrodes 134 on the paddle or lead to stimulate nerve fibers, muscle fibers, or other body tissues near the stimulation system. A processor 204 is generally included to control the timing and electrical characteristics of the stimulation system. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. In some embodiments, the processor may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 208 that, for example, allow modification of pulse characteristics. In the illustrated embodiment, the processor 204 is coupled to a receiver 202 which, in turn, is coupled to the optional antenna 218. This allows the processor to receive instructions from an external source to, for example, direct the pulse characteristics and the selection of electrodes, if desired.

In one embodiment, the antenna 218 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the stimulation system. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 218 and receiver 202 can be used to modify or otherwise direct the operation of the stimulation system. For example, the signals may be used to modify the pulses of the stimulation system such as modifying one or more of pulse duration, pulse frequency, pulse waveform, and pulse strength. The signals may also direct the stimulation system to cease operation or to start operation or to start charging the battery. In other embodiments, the stimulation system does not include an antenna 218 or receiver 202 and the processor 204 operates as programmed.

Optionally, the stimulation system may include a transmitter (not shown) coupled to the processor and antenna for transmitting signals back to the telemetry unit 206 or another unit capable of receiving the signals. For example, the stimulation system may transmit signals indicating whether the stimulation system is operating properly or not or indicating when the battery needs to be charged. The processor may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable lead, comprising:
   an expandable paddle body, wherein the paddle body is configured for percutaneous implantation through an introducer followed by expansion of a volume of the paddle body by at least 10%, wherein the paddle body comprises an expandable mesh configured and arranged to permit expansion of the mesh after implantation of the lead; and a plurality of electrodes disposed on the paddle body and configured and arranged to provide electrical stimulation to adjacent tissue when implanted with the lead coupled to a control module.

2. The implantable lead of claim 1, wherein the paddle body is configured and arranged for expansion by inserting a fluid into the paddle body.

3. The implantable lead of claim 2, wherein the paddle body is configured and arranged for deflation over a period of time after expansion.

4. The implantable lead of claim 1, wherein at least one of the electrodes has an identification feature to allow determination of an orientation of implantation of the lead by observation of the identification feature.

5. The implantable lead of claim 4, wherein the identification feature is at least one indentation asymmetrically positioned in a shape of the at least one electrode.

6. A kit for implanting a lead, comprising:
the implantable lead of claim 1; and
an introducer through which the paddle body of the lead can be percutaneously implanted into tissue of a body and then withdrawn from the lead.

7. The kit of claim 6, wherein the introducer is a needle introducer that comprises a plurality of windows configured and arranged to permit stimulation of tissue adjacent to at least one of the plurality of windows by alignment of at least one of the electrodes of the implantable lead with the at least one of the plurality of windows while the lead is still disposed within the needle introducer.

8. A kit for implanting a lead, comprising:
a lead comprising a paddle body with a plurality of electrodes disposed on the paddle body, wherein at least one of the electrodes has an identification feature to allow determination of an orientation of implantation of the lead by observation of the identification feature; and
a needle introducer with a non-circular, closed-path, transverse cross section through which the paddle body of the lead can be percutaneously implanted into tissue of a body and then withdrawn from the lead, wherein the needle introducer comprises a plurality of windows configured and arranged permit stimulation of tissue adjacent to at least one of the plurality of windows by alignment of at least one of the electrodes of the lead with the at least one of the plurality of windows while still disposed within the needle introducer.

9. The kit of claim 8, wherein the identification feature is at least one indentation in a shape of the at least one electrode.

10. An implantable lead, comprising:
a paddle body; and
a plurality of electrodes disposed on the paddle body and configured and arranged to provide electrical stimulation to adjacent tissue when implanted with the lead coupled to a control module, wherein the paddle body is configured for percutaneous implantation and when implanted the lead is configured and arranged so that a position or orientation of the plurality of electrodes relative to a portion of the paddle body immediately adjacent to the electrodes is alterable.

11. The implantable lead of claim 10, further comprising a plurality of hinges, wherein the plurality of electrodes are each coupled to a one of the plurality of hinges that allows the electrode to change position or orientation with respect to the portion of the paddle body immediately adjacent to the electrodes.

12. A method for percutaneous implantation of a lead of an electrical stimulation system, the method comprising:
inserting an introducer through skin of a patient with at least a portion of the lead disposed in the introducer, the lead comprising a paddle body with a plurality of electrodes disposed on the paddle body;
positioning the lead near tissue to be stimulated including observing an identification feature on at least one of the electrodes to determine an orientation of implantation of the lead, wherein the identification feature comprises at least one indentation asymmetrically positioned on the shape of the at least one of the electrodes;
withdrawing the introducer leaving the lead implanted in the patient; and
expanding a volume of the paddle body by at least 10% after implanting the lead.

13. The method of claim 12, wherein expanding the paddle body comprises introducing a fluid into the paddle body.

14. The method of claim 12, further comprising deflating the paddle body after a period of time has elapsed from expanding the paddle body.

15. The method of claim 12, wherein positioning the lead comprises stimulating adjacent tissue through windows in the introducer using electrodes on the lead which are aligned with the windows in the introducer.

16. The method of claim 12, wherein the introducer is a needle introducer and the introducer has a non-circular, closed-path, transverse cross-section through which the paddle body of the lead can be percutaneously implanted into tissue of a body.

* * * * *